(12) United States Patent
Zeiner et al.

(10) Patent No.: US 12,256,929 B1
(45) Date of Patent: Mar. 25, 2025

(54) COMPRESSION CAM RETAINERS FOR STAPLE CARTRIDGES WITH IMPLANTABLE ADJUNCTS

(71) Applicant: CILAG GMBH INTERNATIONAL, Zug (CH)

(72) Inventors: Mark Zeiner, Loveland, OH (US); Sarah Alexandra Scully, Cincinnati, OH (US); Christopher Seow, Cincinnati, OH (US); Madelaine Franzoni, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 0 days.

(21) Appl. No.: 18/505,703

(22) Filed: Nov. 9, 2023

(51) Int. Cl.
*A61B 17/072* (2006.01)

(52) U.S. Cl.
CPC ........... *A61B 17/07207* (2013.01); *A61B 2017/07271* (2013.01); *A61B 2017/07278* (2013.01)

(58) Field of Classification Search
CPC .... A61B 17/07207; A61B 2017/07271; A61B 2017/07278
See application file for complete search history.

(56) References Cited

U.S. PATENT DOCUMENTS 9,351,730 B2  5/2016 Schmid

*Primary Examiner* — Michelle Lopez
(74) *Attorney, Agent, or Firm* — TROUTMAN PEPPER LOCKE LLP

(57) ABSTRACT

Retainers and retainer systems for staple cartridges with implantable adjuncts are disclosed. The retainers and retainer systems enable a compressive force to be applied to implantable adjuncts on staple cartridges. The retainer is movable through a range of motion relative to the staple cartridge, and movement of a retainer cam through a track compresses the implantable adjunct against the deck of the elongate body.

20 Claims, 15 Drawing Sheets

COMPRESSION CAM RETAINERS FOR STAPLE CARTRIDGES WITH IMPLANTABLE ADJUNCTS

FIELD OF INVENTION

The present disclosure generally relates to retainers and retainer systems for staple cartridges with implantable adjuncts. More specifically, the present disclosure relates to retainers and retainer systems that enable a compressive force to be applied to implantable adjuncts on staple cartridges.

BACKGROUND

Stapling is a crucial aspect of many surgical procedures, such as gastrointestinal, thoracic, and gynecological surgeries. Staple cartridges used in these stapling procedures may include an implantable adjunct on the deck of the cartridge. Care must be taken to ensure the implantable adjunct is properly adhered to the deck so that it is not dislodged from the deck during shipment or, importantly, during surgery before the adjunct is positioned at the treatment site.

SUMMARY

It is an object of the present designs to provide devices and methods to meet the above-stated needs. The designs can be for systems and devices for protecting an implantable adjunct on a staple cartridge, while also providing structure to allow compression of the adjunct to the deck of the staple cartridge before being used in surgery.

The instant disclosure describes a staple cartridge. The staple cartridge includes an elongate body. The elongate body includes a deck and defines a plurality of staple pockets, each of the staple pockets accessible via an opening defined by the deck. The cartridge comprises an implantable adjunct removably secured to the deck. The cartridge comprises a track and a retainer removably securable to the elongate body, the retainer comprising a retainer cam engageable with the track. The retainer is movable through a range of motion relative to the elongate body while the retainer is secured to the elongate body. The track further defines a movement path for the retainer with respect to the elongate body. With the retainer secured to the elongate body, and the implantable adjunct positioned intermediate the retainer and the elongate body, a movement of the retainer cam through the track from a first cam position to a second cam position moves the retainer toward the elongate body thereby compressing the implantable adjunct against the deck of the elongate body.

The instant disclosure describes a method of causing a retainer to compress an implantable adjunct against a deck of an elongated body of a staple cartridge. The method includes actuating a retainer cam through a range of motion defined by a track to actuate a retainer of a staple cartridge. The method includes moving, via the actuation, the retainer cam from a first cam position to a second cam position, thereby causing the retainer to compress an implantable adjunct against a deck of an elongate body of the staple cartridge.

Other aspects of the present disclosure will become apparent upon reviewing the following detailed description in conjunction with the accompanying figures. Additional features or manufacturing and use steps can be included as would be appreciated and understood by a person of ordinary skill in the art.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation. It is expected that those of skill in the art can conceive of and combine elements from multiple figures to better suit the needs of the user.

DETAILED DESCRIPTION

Specific examples of the present invention are now described in detail with reference to the Figures, where identical reference numbers indicate elements which are functionally similar or identical. The examples provide solutions for staple cartridge systems that include an implantable adjunct. An implantable adjunct can be used in stapling surgery to account for differing tissue thicknesses across the length of the stapling surface. For instance, a length of tissue clamped in an end effector of a surgical instrument may by thicker at one end of the staple cartridge than at the other end. However, the staple cartridge may be loaded with staples of a single length, meaning the staples may be properly sized for the thicker section of tissue, but may be too long for the thinner section of tissue. If the staples are too long, proper compression of the tissue at the staple site may be compromised, leading to undesired bleeding. An implantable adjunct can account for this differing tissue thickness by providing support for the thinner sections of tissue. Where the tissue is thick, the implantable adjunct can be compressed almost all the way down to a negligible thickness since no additional thickness is needed to account for the staple length. Where the tissue is thin, the implantable adjunct is not as compressed, meaning the adjunct provides the additional thickness needed to account for the staple length, thereby providing proper compression in that section of the tissue.

The implantable adjunct must be properly, yet reversibly, adhered to the deck of the staple cartridge so that it does not become dislodged during shipment or, importantly, during the surgical procedure. For instance, during surgery the staple cartridge is loaded into an end effector of a cutter/stapler surgical instrument, sent through a cannula to a surgical site, traversed through and around tissue, and then positioned at the target tissue site that will be cut and stapled by the surgical instrument. If the implantable adjunct is not properly adhered to the deck of the staple cartridge, it may become dislodged from the deck during this procedure. The adjunct is adhered to the cartridge deck with an attachment material, which needs to be sticky or tacky enough to keep the adjunct adhered to the deck, but not so sticky that it is difficult to detach from the deck after the stapling procedure is completed. As such, the present retainer systems provide solutions that ensure the adjunct is properly adhered to the staple cartridge right before the staple cartridge is positioned at the treatment site. These systems provide such solutions by incorporating retainers and retainer systems that enable a temporary compressive force to be applied to implantable adjuncts on staple cartridges before they are used in surgery.

Figure 1:
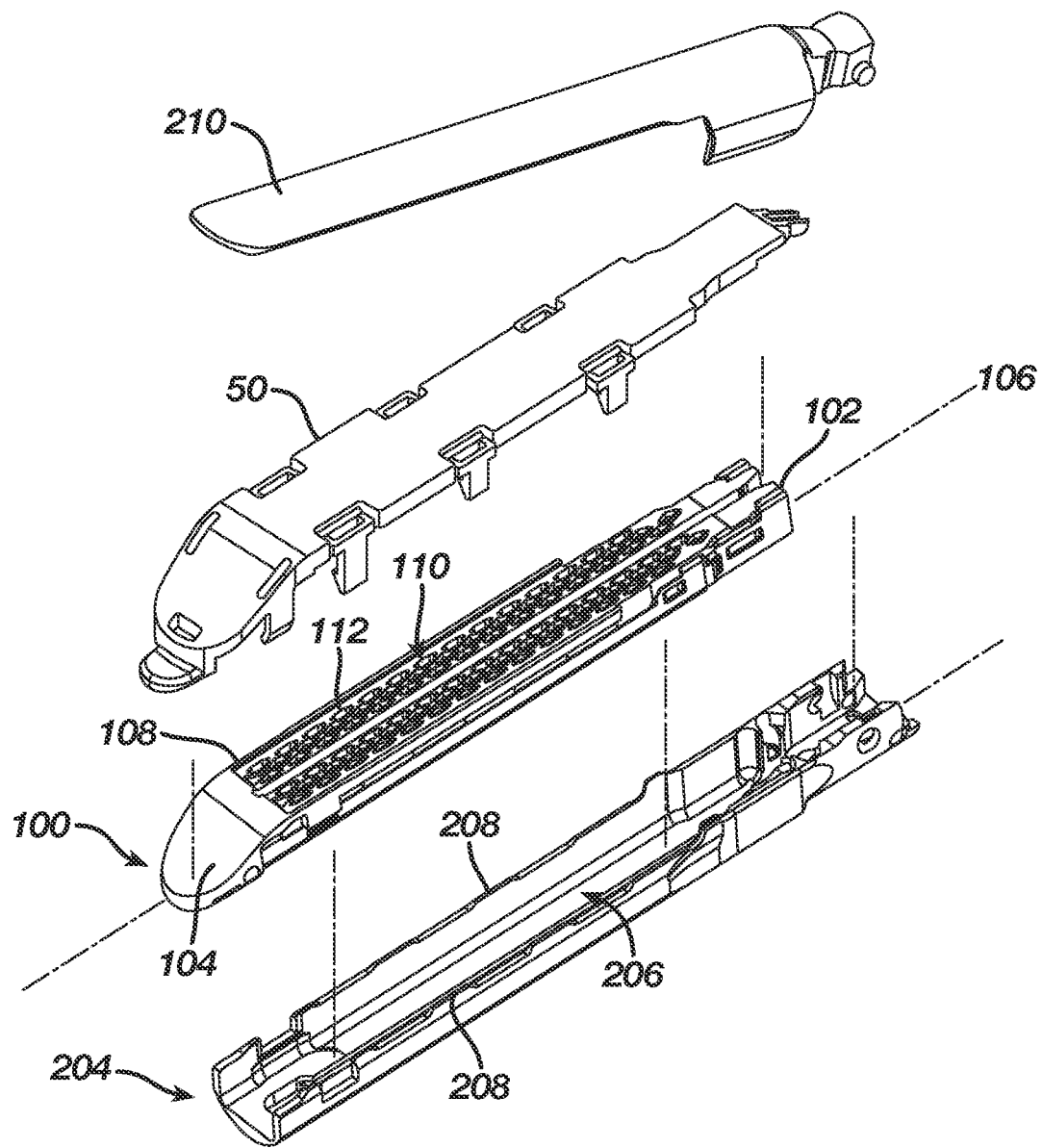
FIG. 1 is a perspective view of a replaceable staple cartridge without an adjunct.

Referring now to the figure, FIG. 1 shows an exploded view of a prior staple cartridge 100 that does not include an implantable adjunct on deck 108 thereof. In these prior examples, retainer 50 can be attached to staple cartridge 100 from proximal end 102 to distal end 104 to ensure that staples within various staple pockets 110 do not fall out of openings 112 within deck 108. Retainer 50 has a function of preventing staples from falling out before staple cartridge 100 is positioned within channel 206 of first jaw frame 204 of end effector 202. Retainer 50 is simply removed when staple cartridge 100 is inserted between channel rails 208 of channel 206.

Figure 2A:
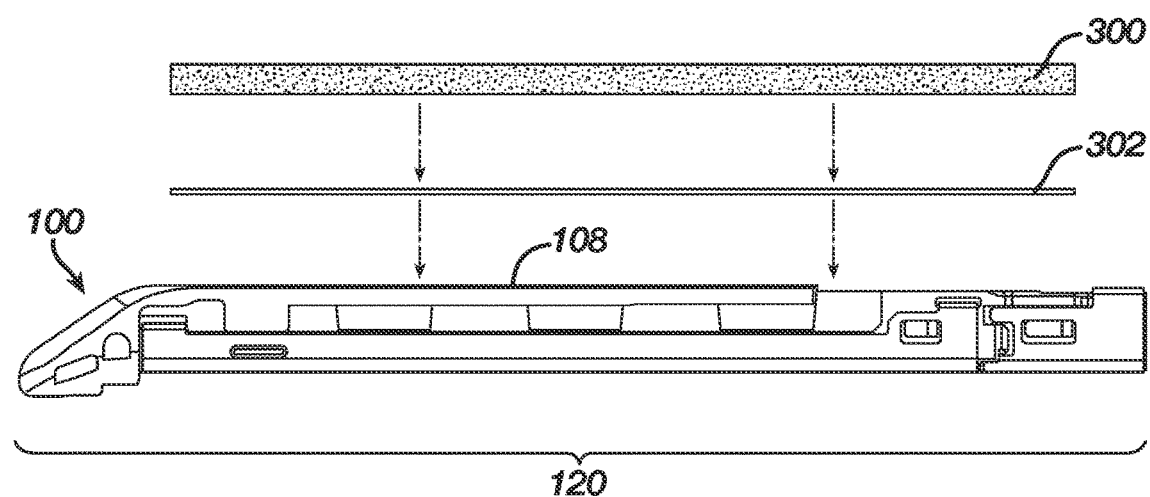
FIG. 2A is a schematic showing a replaceable staple cartridge, an attachment material, and an implantable adjunct, according to aspects of the present disclosure.
Figure 2B:
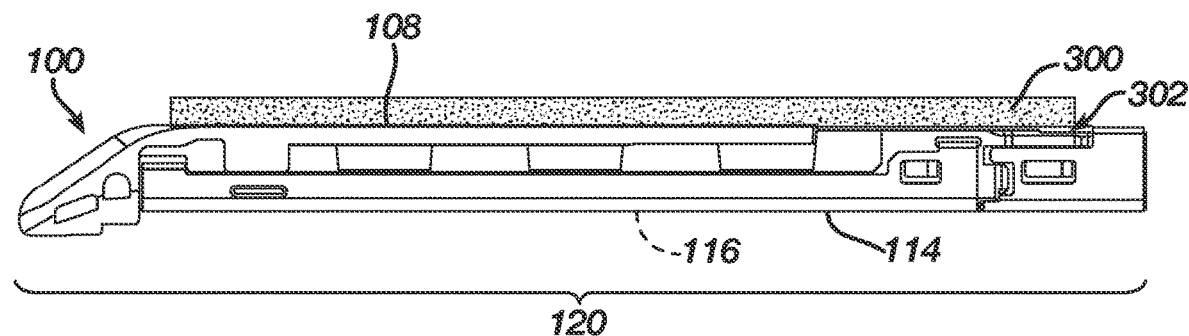
FIG. 2B is a schematic showing the replaceable staple cartridge, attachment material, and implantable adjunct of FIG. 2A assembled, according to aspects of the present disclosure.
Figure 2C:
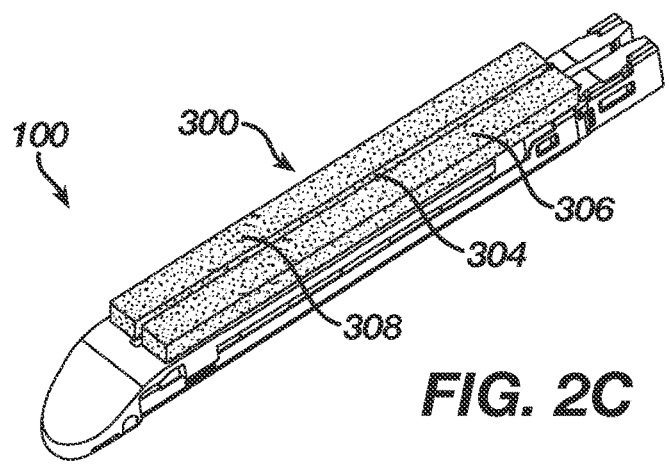
FIG. 2C is a perspective view of the assembled staple cartridge, attachment material, and implantable adjunct shown in FIG. 2B, according to aspects of the present disclosure.

FIGS. 2A-2C illustrate staple cartridges that include an implantable adjunct. As seen in the exploded view of FIG. 2A, the system includes staple cartridge 100 (which is substantially similar to the staple cartridge shown in FIG. 1) and implantable adjunct 300 which is adhered to deck 108 that is positioned along elongate body 120 of staple cartridge 100. Implantable adjunct 300 can be adhered to staple cartridge 100 with attachment material 302. As described above, attachment material 302 can provide sufficient adhesion for implantable adjunct 300 to remain adhered to deck 108 when being positioned at the treatment site, but the adhesion does not impair the ability of implantable adjunct 300 from being detached from deck 108 when being implanted. In some instances, attachment material can be an adhesive, adhesive strip, double-sided tape, and the like. The implantable adjunct 300 can also be adhered directly to deck 108. FIG. 2B shows implantable adjunct 300 adhered to deck 108 via attachment material 302. FIG. 2C is a perspective view of implantable adjunct 300 adhered to deck 108. For background, the staples of the systems described herein are fired through implantable adjunct 300 during the stapling procedure. In some instances, implantable adjunct 300 can include sled groove 304 within length 350 of the adjunct. Sled groove 304 provides a path for a knife (not shown in figures) to traverse such that the knife does not need to cut through implantable adjunct 300, thereby preserving the edge on the knife. When implantable adjunct 300 includes sled groove 304, implantable adjunct 300 can be considered to be separated into adjunct first side 306 and adjunct second side 308. In some examples, adjunct 300 can include laminated layers, such as a foam and/or porous material laminated with a mesh material, wherein the sled groove 304 is disposed in the foam and/or porous material but the mesh material remains intact. In other examples, adjunct 300 can include a film layer and/or a mesh layer. The film layer can comprise material commonly used with absorbable monofilament sutures and can be heat processed with a mesh layer to act as a bonding agent to hold the mesh and foam of the adjunct 300 together.

Figure 3A:
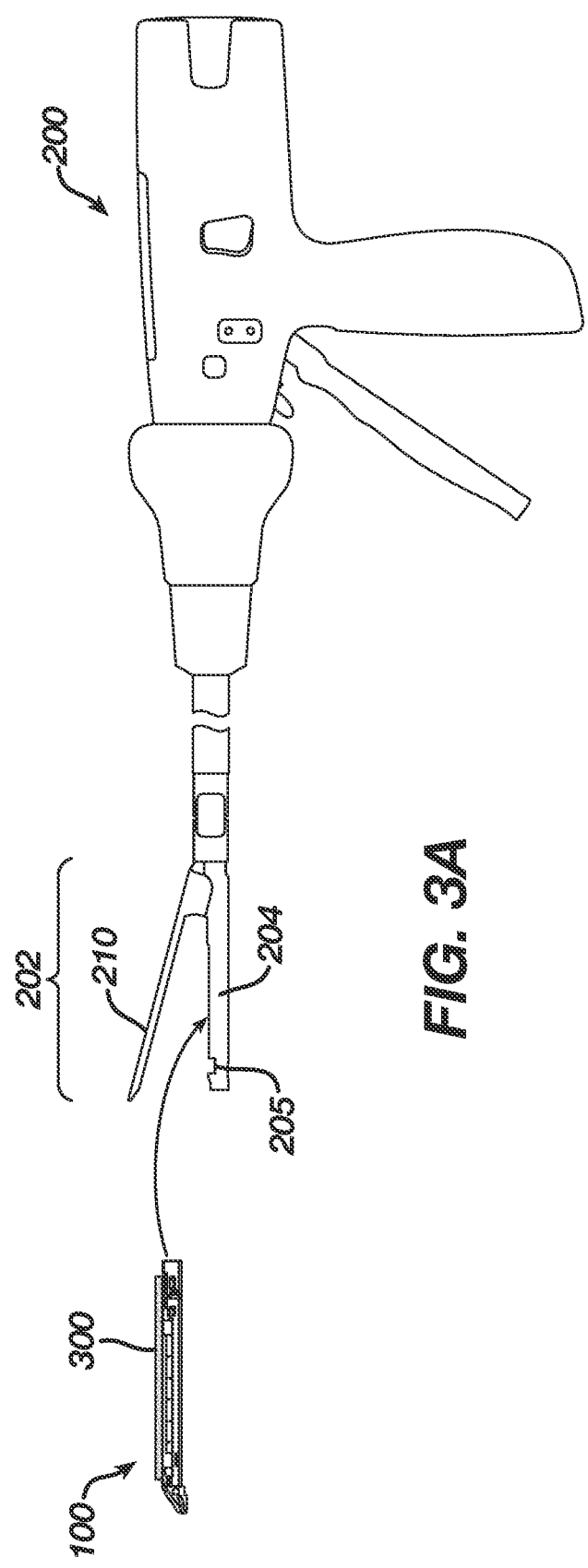
FIG. 3A is a side-view schematic of a staple cartridge being loaded into a surgical instrument, according to aspects of the present disclosure.

FIG. 3A is a side-view schematic of staple cartridge 100 being loaded into a surgical instrument, i.e., surgical instrument 200. Staple cartridge 100 is loaded into end effector 202 before being positioned at the treatment site. As described above, staple cartridge 100 is inserted into first jaw frame 204. Anvil 210 clamps down toward staple cartridge 100 during the stapling procedure. Once the tissue is stapled, anvil 210 opens to leave the staples and adjunct attached to the tissue. Staple cartridge 100 remains in first jaw frame 204 as surgical instrument 200 is removed from the treatment site. In other examples, the entire end effector 202 with staple cartridge 100 can be preassembled and attached to surgical instrument 200 (embodiment not illustrated). The examples described below can be used with the preassembled embodiment as well.

Figure 3B:
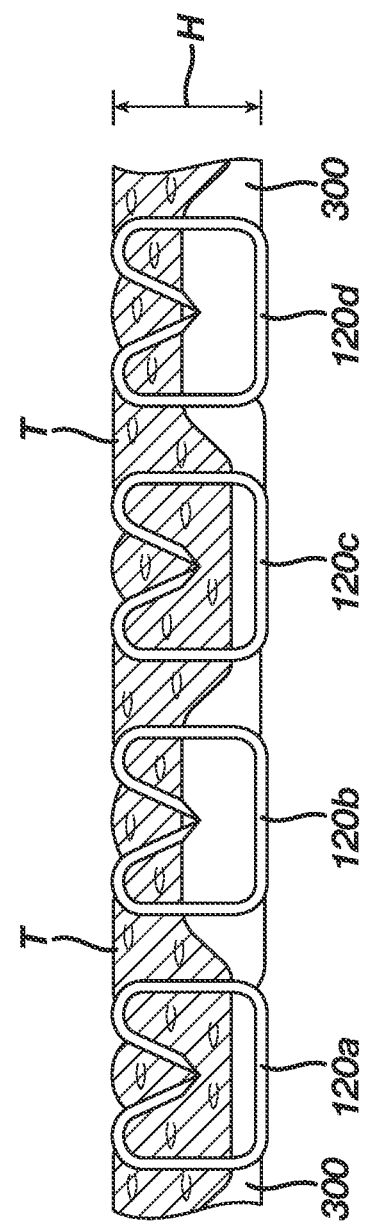
FIG. 3B is a schematic of an implantable adjunct stapled to tissue, according to aspects of the present disclosure.
Figure 4A:
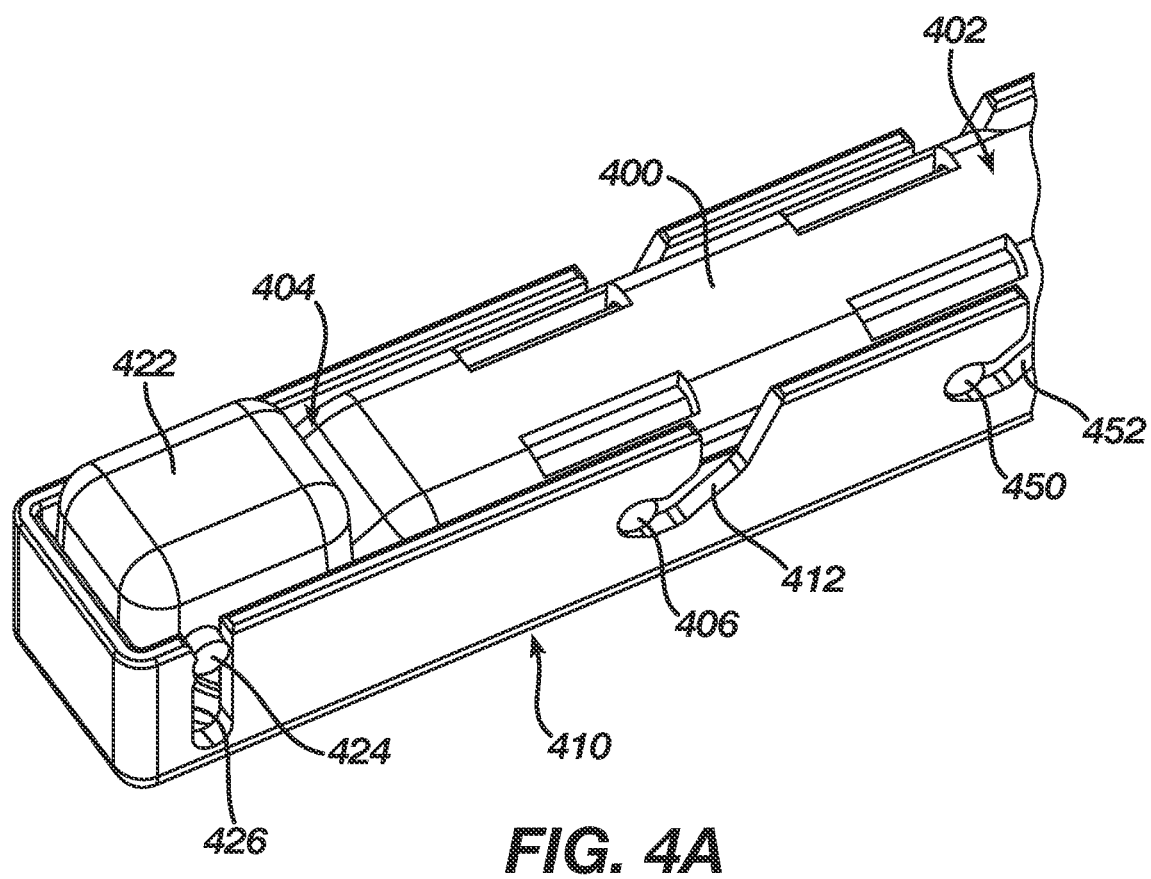
FIG. 4A is atop perspective view of a staple cartridge inside abase and retainer, wherein the retainer is moveable a first position to a second, compressive position via movement through a cam track, according to aspects of the present disclosure.
Figure 4B:
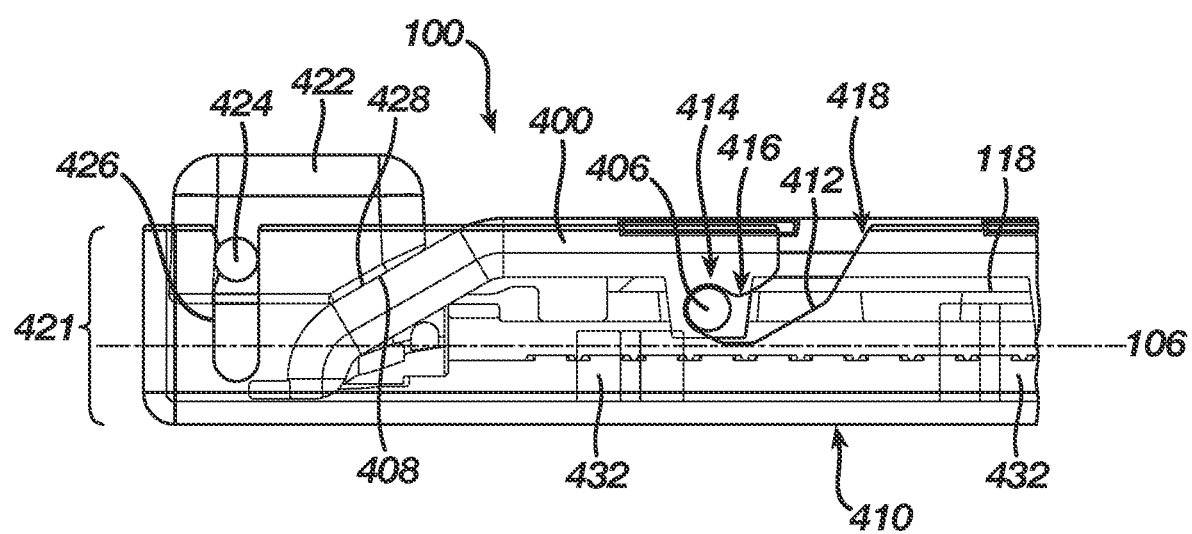
FIG. 4B is a side, partially transparent view of the staple cartridge, retainer, and base of FIG. 4A, wherein the retainer is at a first cam position within the cam track, according to aspects of the present disclosure.
Figure 4C:
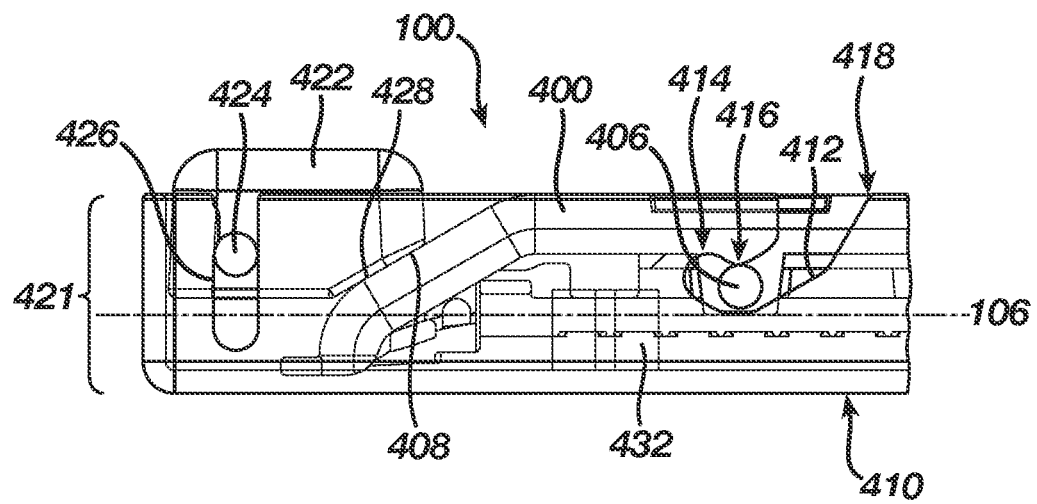
FIG. 4C is a side, partially transparent view of the staple cartridge, retainer, and base of FIGS. 4A and 4B, wherein the retainer is at a second cam (compressed) position within the cam track, according to aspects of the present disclosure.
Figure 4D:
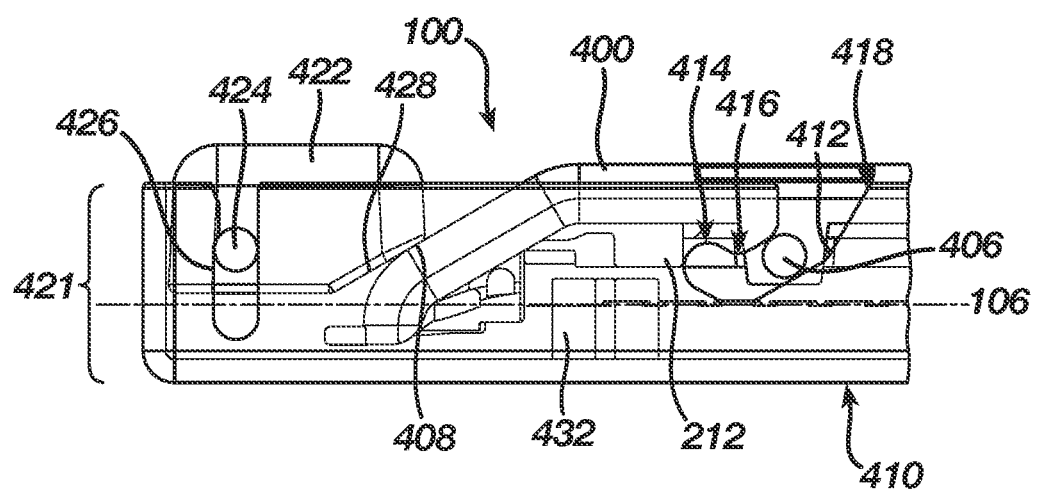
FIG. 4D is a side, partially transparent view of the staple cartridge, retainer, and base of FIGS. 4A-4C, wherein the retainer is at a third position wherein the cam is resting in the cam track just before a track opening, according to aspects of the present disclosure.
Figure 4E:
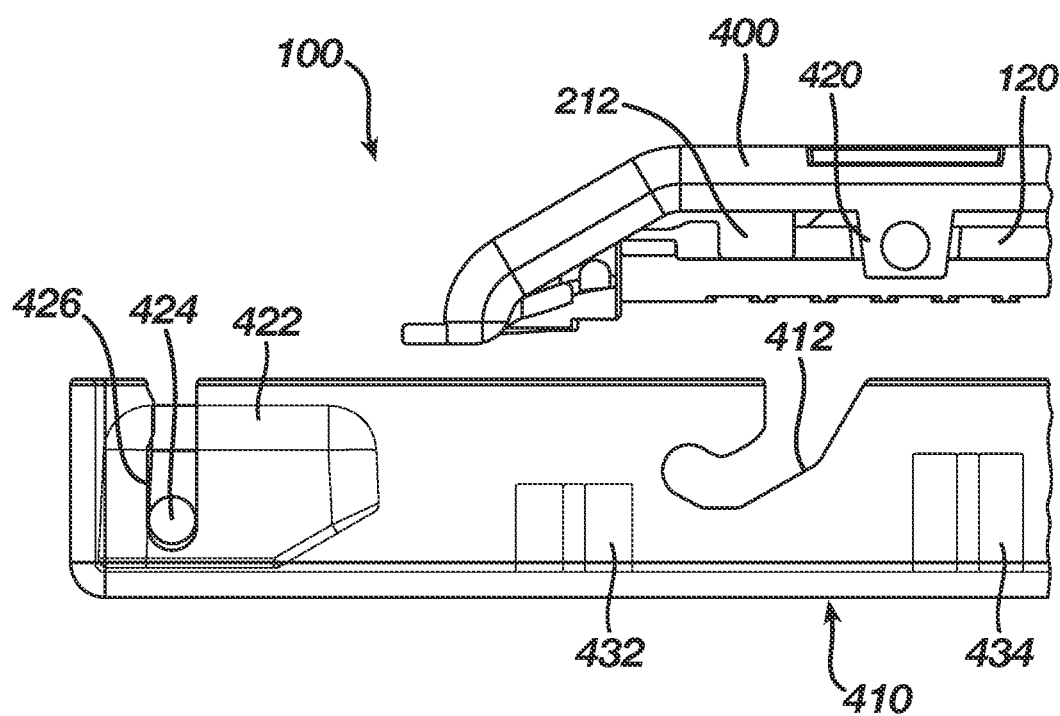
FIG. 4E is a side, partially transparent view of the staple cartridge, retainer, and base of FIGS. 4A-4D, wherein the retainer is released from the base, according to aspects of the present disclosure.
Figure 5A:
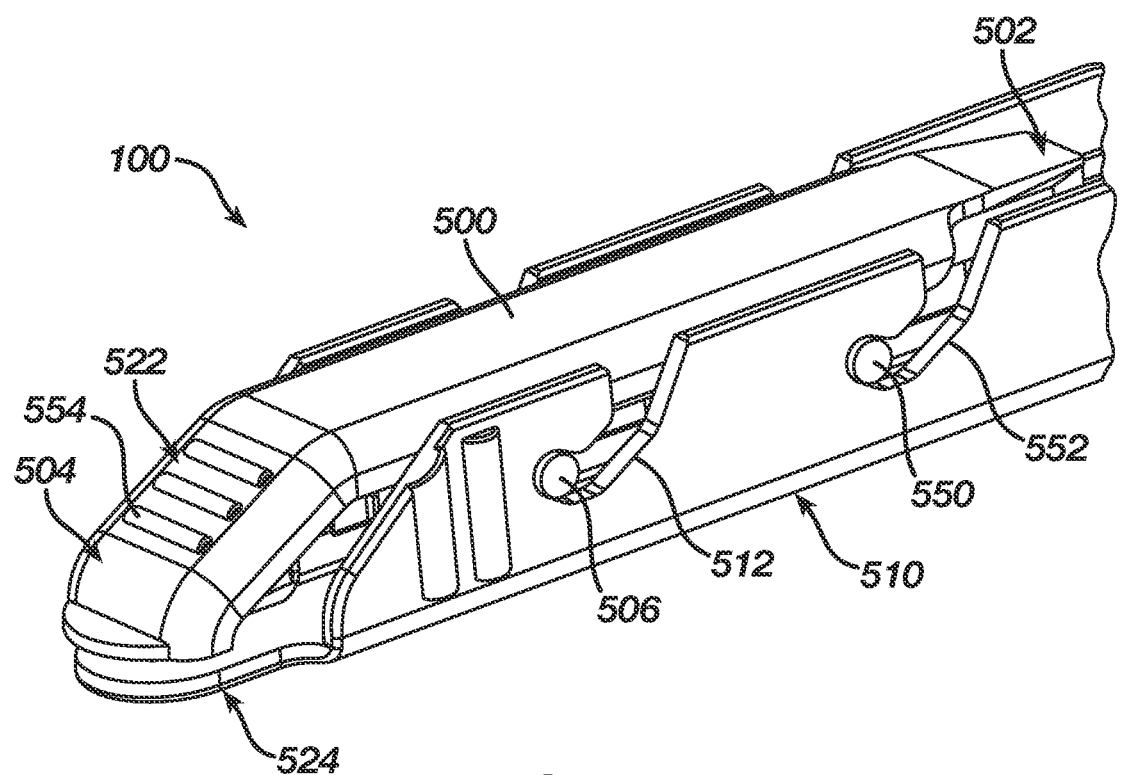
FIG. 5A is atop perspective view of a staple cartridge inside abase and retainer, wherein the retainer is moveable a first position to a second, compressive position via movement through a cam track, according to aspects of the present disclosure.
Figure 5B:
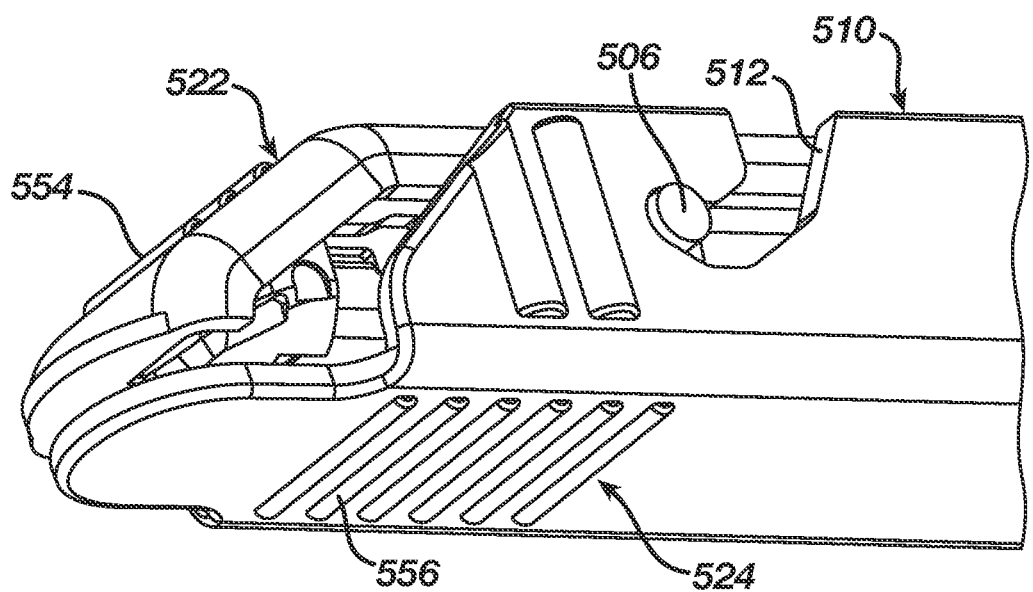
FIG. 5B is a bottom perspective view of a staple cartridge shown in FIG. 5A, according to aspects of the present disclosure.
Figure 5C:
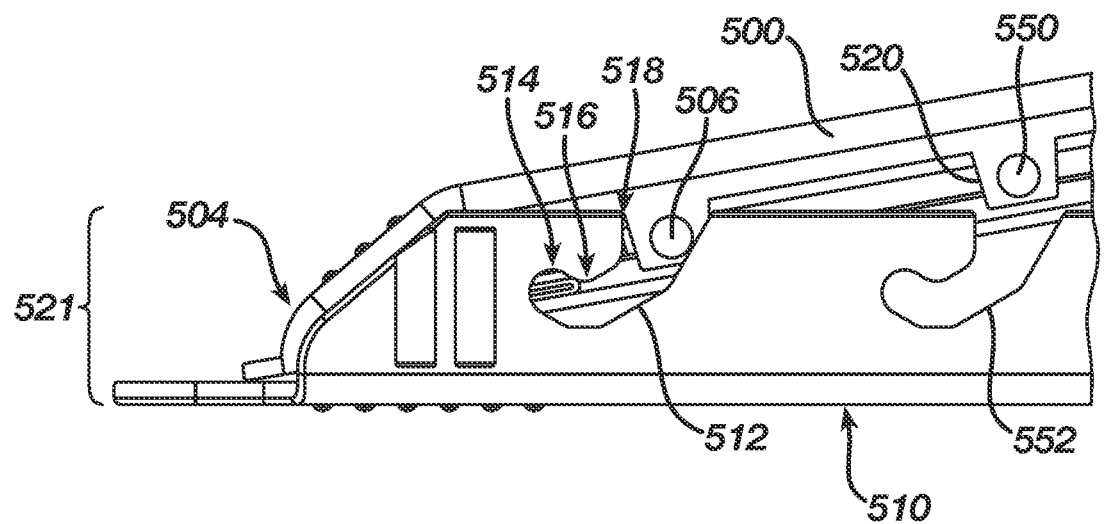
FIG. 5C is a side view of the staple cartridge, retainer, and base of FIGS. 5A and 5B, wherein the retainer is moved to a position such that the cam can exit the cam track, according to aspects of the present disclosure.
Figure 6A:
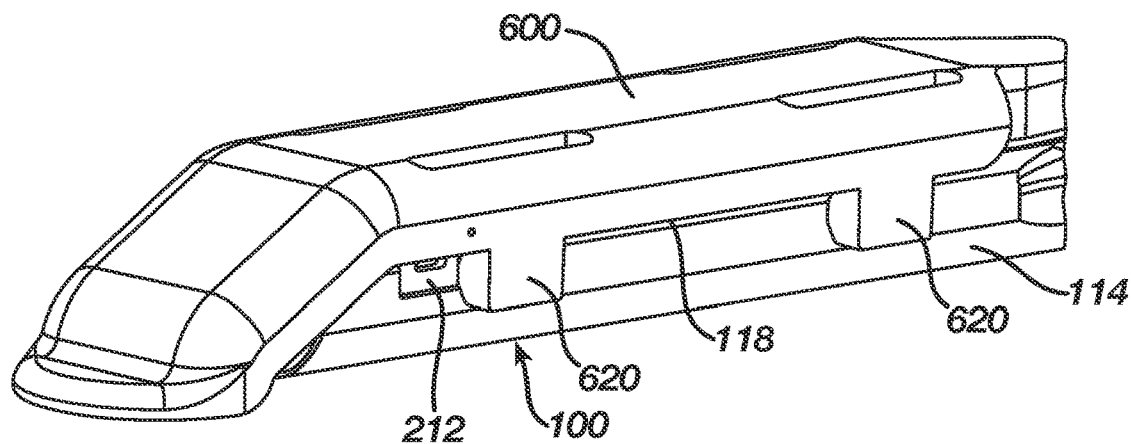
FIG. 6A is a top perspective view of a staple cartridge and a retainer with a cam arm pivotably attached to the retainer, according to aspects of the present disclosure.
Figure 6B:
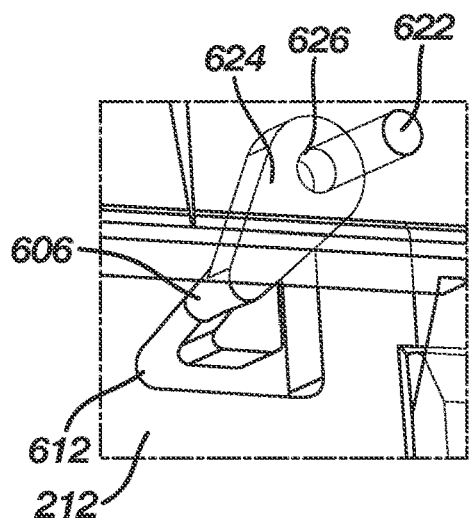
FIG. 6B is a detail view of the cam and cam arm of the retainer shown in FIG. 6A, according to aspects of the present disclosure.
Figure 6C:
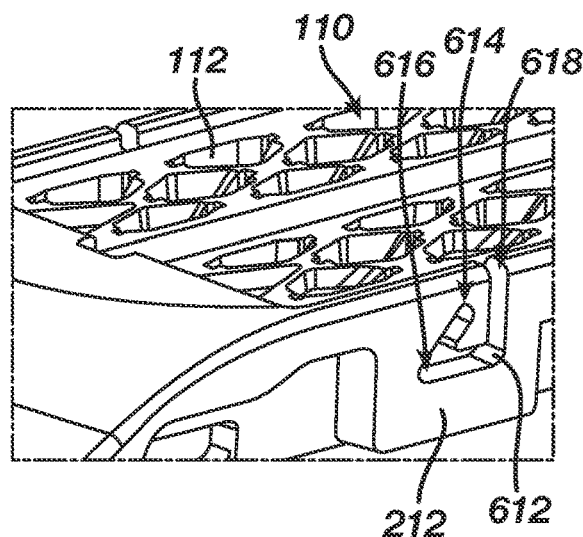
FIG. 6C is a detail view of the cam track of the cartridge shown in FIGS. 6A and 6B, according to aspects of the present disclosure.
Figure 6D:
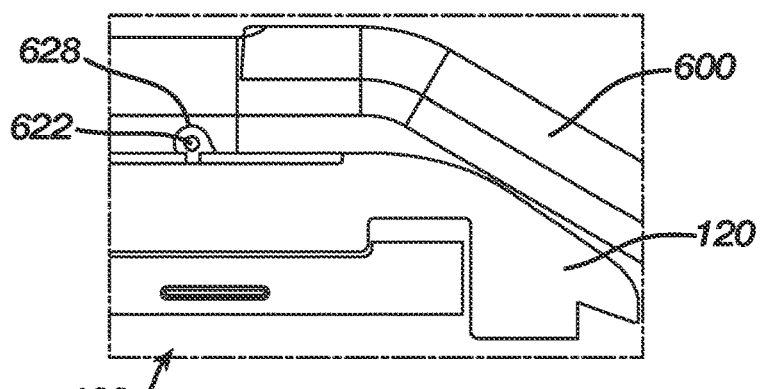
FIG. 6D is a detail view of the cam and cam arm of the retainer shown in FIGS. 6A-6C, according to aspects of the present disclosure.
Figure 6E:
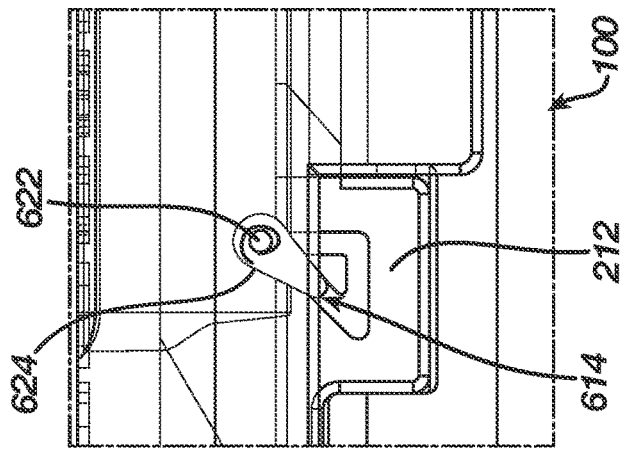
FIGS. 6E-6G are detail views of the cam and cam arm of FIGS. 6A-6D in a first position (FIG. 6E), a second position (FIG. 6F), and a third, releasable position (FIG. 6G), according to aspects of the present disclosure.
Figure 6F:
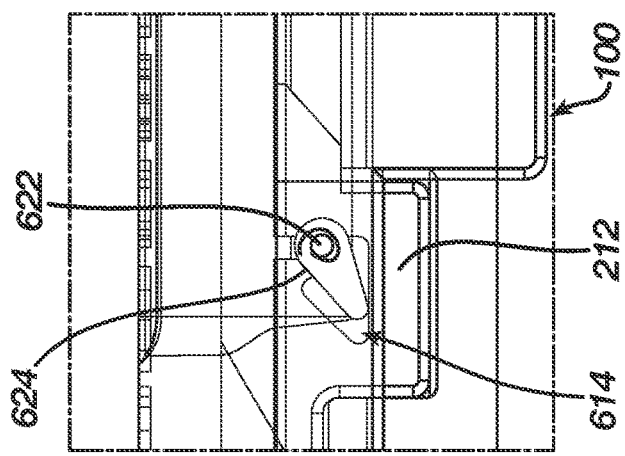
Figure 6G:
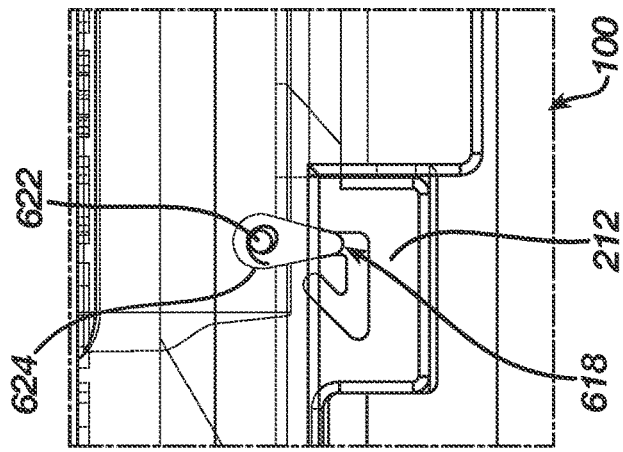
Figure 6H:
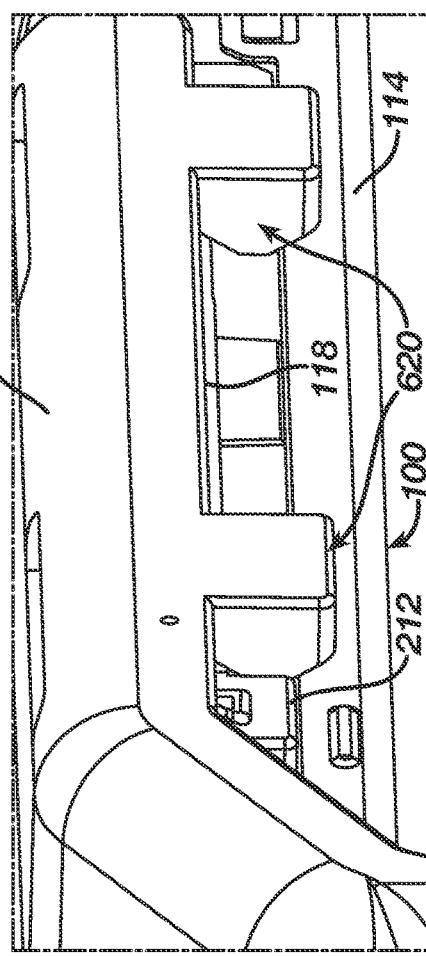
FIG. 6H is a perspective view of the staple cartridge and retainer of FIGS. 6A-6G, according to aspects of the present disclosure.

Although FIG. 3A shows staple cartridge 100 without a retainer attached thereto, the example retainers (i.e., retainer 400) described herein can be inserted into first jaw frame 204 while attached to said staple cartridge 100 (see the construct in FIGS. 4E, 5C, 6H, for example). As stated above, implantable adjunct 300 can account for this differing tissue thickness by providing buttress support for the thinner sections of tissue. Where the tissue is thick, implantable adjunct 300 can be compressed almost all the way down to a negligible thickness since no additional thickness is needed to account for the staple length. Where the tissue is thin, the implantable adjunct 300 is not as compressed, meaning the adjunct provides the additional thickness needed to account for the staple length, thereby providing proper compression in that section of the tissue. FIG. 3B is a schematic showing the implantable adjunct 300 stapled to tissue (T) having different thickness. The individual staples 120*a,b,c,d* have the same height (H), so the implantable adjunct 300 fills in the space for thinner sections of tissue (i.e., the tissue (T) shown at staples 120*b* and 120*d*). For thicker sections of tissue (i.e., the tissue (T) shown at staples 120*a* and 120*c*), the implantable adjunct 300 is more compressed as the staples do not need the additional space (i.e., height) filled in by the implantable adjunct 300.

Referring now to FIGS. 4A-4E, the example implementation shows a staple cartridge and retainer system that can protect an adjunct during shipment of the staple cartridge and also provide a compressive force to the adjunct. The system shown includes retainer 400 and base 410. Retainer 400 can be releasably secured to staple cartridge 100, and retainer 400 can also be independently releasably secured to base 410. As such, base 410 can act as a disposable protector for staple cartridge 100 during shipment, and then can be detached from retainer 400 when the cartridge is ready for surgery. Retainer 400 can be detached from staple cartridge 100 once the cartridge is loaded into first jaw frame 204 (see FIG. 3A).

Referring again to retainer 400 of FIG. 4A, retainer 400 is removably securable to elongate body 120 of staple cartridge 100. Retainer 400 includes a retainer cam 406 that is engageable with track 412 in base 410. Retainer 400 is moveable through a range of motion relative to elongate body 120 while retainer 400 is secured to elongate body 120, as retainer cam 406 will move through the path provided by track 412 as retainer 400 is moved through its range of motion. Movement of retainer cam 406 through track 412 from a first cam position 414 to a second cam position 416 moves retainer 400 toward elongate body 120, thereby compressing implantable adjunct 300 against deck 108 of elongate body 120. It is contemplated that the compression of the implantable adjunct 300 could be in the order of approximately 50% of its thickness, or in the alternative to just before a solid stack height wherein the compression implantable adjunct 300 is just less than a maximum amount of compression—i.e., to a point where the foam will not compress any further. To further illustrate, in the first cam position 414 (see FIG. 4B), retainer cam 406 is positioned such that retainer 400 is at a predetermined distance away from base 410 and implantable adjunct 300 is not compressed. This can be the configuration in which the system is shipped. In the second cam position 416 (see FIG. 4C), retainer cam 406 is positioned such that retainer 400 moved toward base 410 such that implantable adjunct 300 becomes compressed. At the same time, this example causes retainer 400 to slide axially with respect to longitudinal axis 106 of elongate body 120 (i.e., actuating the retainer/base causes two-dimensional movement-compression and axial sliding). The first cam position 414 is higher with respect to height 421 of base 410 than is second cam position 416. After retainer cam 406 passes the second cam position 416 (see FIG. 4D), retainer cam 406 moves toward track opening 418 such that retainer 400 can be removed from base 410 (see FIG. 4E). Base 410 is stationary with respect to elongate body 120 during the movement of retainer cam 406 through track 412 from the first cam position 414, to the second cam position 416, to the track opening 418. As is shown in FIG. 4A, retainer 400 can include second cam 450, which is substantially similar to retainer cam 406. Base 410 can include second track 452, which is substantially similar to track 412. Having another cam and track closer to proximal end 402 of retainer 400 can enable uniform compression across the entire length of implantable adjunct 300.

The example retainer system shown in FIGS. 4A-4E comprises actuator 422 positioned proximate distal end 404 of retainer 400. Actuation of actuator 422 causes retainer cam 406 to move through track 412 and further causes retainer 400 to compress the implantable adjunct 300. As actuator 422 is pushed inwardly (down in FIG. 4B, for example) toward base 410, actuator cam 424 on actuator 422 tracks through actuator track 426 on base 410, constraining actuator 422 to move only in that linear direction. As actuator 422 moves through actuator track 426, actuator ramp 428 on actuator 422 will slidably engage with retainer ramp 408 at distal end 404 of retainer 400, thereby causing retainer 400 to both compress implantable adjunct 300 and slide axially with respect to longitudinal axis 106 of elongate body 120. In other examples, the actuator track 426 does not need to be linear or "vertical" as illustrated. The actuator track 426 can be shaped to apply both a downward and a longitudinal force based on the actuator track 426 regardless of the shape of an actuator ramp 428 and a retainer ramp 408.

In certain implementations, and as shown in FIG. 4E, base 410 includes base lug shoulder 432 and/or includes base channel shoulder 434. These features can be used to ensure that retainer 400 is not over compressed onto staple cartridge 100, which could deform the cartridge before inserting it into end effector 202 (see FIG. 3A). Base lug shoulder 432 is positioned within base 410 to align with lug 212 of cartridge 100; base channel shoulder 434 is positioned within base 410 to align with channel rails 208 of cartridge 100. As retainer cam 406 moves through track 412 to the second cam position 416, base lug shoulder 432 and/or base channel shoulder 434 will come close to or contact their respective feature on cartridge 100 to prevent cartridge 100 from bowing or deforming as the compressive force is applied to implantable adjunct 300.

Retainer 400 shown in FIGS. 4A-4E also includes one or more retention tabs 420 extending from retainer 400. Retention tabs 420 are outwardly deflectable upon seating into first jaw frame 204. Retention tabs 420 can keep retainer 400 connected to staple cartridge 100 until the cartridge/retainer is inserted into first jaw frame 204. For instance, retention tabs 420 can hook onto cartridge rails 118 of staple cartridge 100 (see FIGS. 2A and 2B). Upon insertion into first jaw frame 204, channel rails 208 of first jaw frame 204 will slip between retention tabs 420 and staple cartridge 100 to deflect them outwardly, thereby releasing them from cartridge rails 118 such that retainer 400 can be removed from staple cartridge 100. FIG. 6H, although depicting a different embodiment of a retainer (i.e., retainer 600), provides an illustration of retention tabs (e.g., retention tabs 620) hooked to cartridge rails 118 before being deflected by channel rails 208 of first jaw frame 204.

Referring now to FIGS. 5A-5D, the example shows a staple cartridge and retainer system that can protect an adjunct during shipment of the staple cartridge and also provide a compressive force to the implantable adjunct. Retainer 500 in FIGS. 5A-5D is substantially similar to retainer 400 described with respect to FIGS. 4A-4E, but in this implementation retainer 500 includes retainer grip surface 522. Retainer grip surface 522 can include retainer ridges 554 for improved grip. The retainer system in FIG. 4A also includes base 510, which is similar to base 410. Base 510 includes base grip surface 524. Base grip surface 524 can include base ridges 556 for improved grip. In this implementation, the retainer system does not include a separate actuator (e.g., actuator 422 in FIGS. 4A), but instead the actuation of retainer 500 with respect to base 510 is performed by pushing downwardly and axially on retainer 500. For instance, a user can grip distal end 504 of retainer 500 by retainer grip surface 522, grip base 510 by base grip surface 524, and pinch retainer 500 inwardly (down in FIG. 5A, for example) toward base 510. In doing so, retainer cam 506 will move through the path provided by track 512 as retainer 500 is moved through the range of motion.

Referring again to retainer 500 of FIG. 5A, retainer 500 is removably securable to elongate body 120 of staple cartridge 100. Retainer 500 includes a retainer cam 506 that is engageable with track 512 in base 510. Retainer 500 is moveable through a range of motion relative to elongate body 120 while retainer 500 is secured to elongate body 120, as retainer cam 506 will move through the path provided by track 512 as retainer 500 is moved through the range of motion. Movement of retainer cam 506 through track 512 from a first cam position 514 to a second cam position 516 moves retainer 500 toward elongate body 120, thereby compressing implantable adjunct 300 against deck 108 of elongate body 120. To further illustrate, in the first cam position 514 (see FIGS. 5A and 5B), retainer cam 506 is positioned such that retainer 500 is at a predetermined distance away from base 510 and implantable adjunct 300 is not compressed. This can be the configuration in which the system is shipped. In the second cam position 516 (see FIG. 5C for reference), retainer cam 506 is positioned such that retainer 500 moved toward base 510 such that implantable adjunct 300 becomes compressed. At the same time, this example causes retainer 500 to slide axially with respect to longitudinal axis 106 of elongate body 120 (i.e., actuating the retainer/base causes two-dimensional movement-compression and axial sliding). The first cam position 516 is higher with respect to height 521 of base 510 than is second cam position 516. After retainer cam 506 passes the second cam position 516, retainer cam 506 moves toward track opening 518 such that retainer 500 can be removed from base 510 (this position is shown in FIG. 5C). Base 510 is stationary with respect to elongate body 120 during the movement of retainer cam 506 through track 512 from the first cam position 514, to the second cam position 516, to the track opening 518. As is shown in FIG. 5A, retainer 500 can include second cam 550, which is substantially similar to retainer cam 506. Base 510 can include second track 552, which is substantially similar to track 512. Having another cam and track closer to proximal end 502 of retainer 500 can enable uniform compression across the entire length of implantable adjunct 300.

Figure 5D:
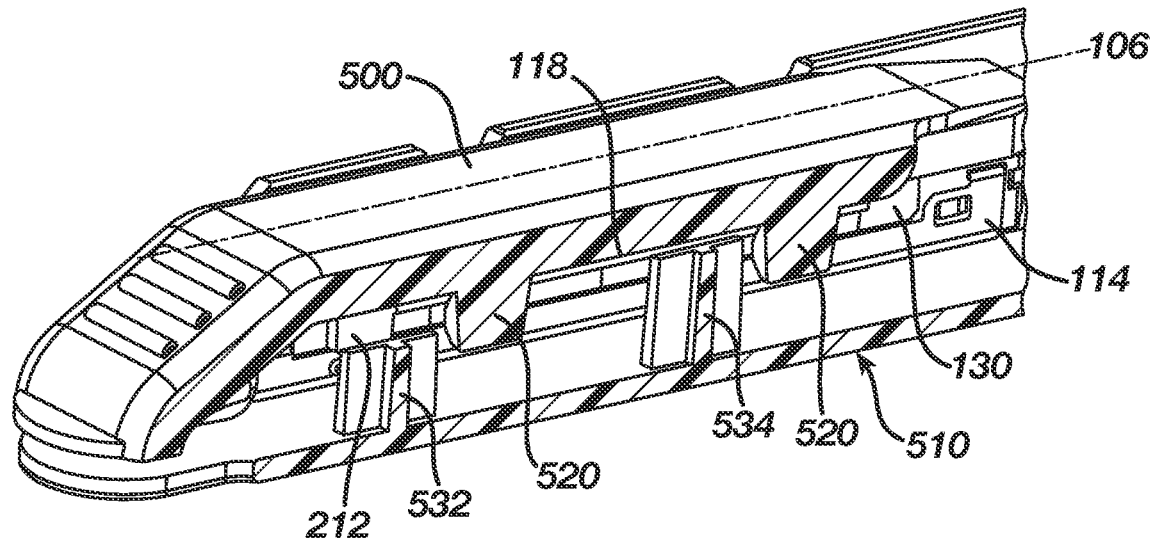
FIG. 5D is a cutaway view of the staple cartridge, retainer, and base of FIGS. 5A-5C, according to aspects of the present disclosure.

In certain implementations, and as shown in FIG. 5D, base 510 includes base lug shoulder 532 and/or includes base channel shoulder 534. These features can be used to ensure that retainer 500 is not over compressed onto staple cartridge 100, which could deform the cartridge before inserting it into end effector 202 (see FIG. 3A). Base lug shoulder 532 is positioned within base 510 to align with lug 212 of cartridge 100; base channel shoulder 534 is positioned within base 510 to align with channel rails 208 of cartridge 100. As retainer cam 506 moves through track 512 to the second cam position 516, base lug shoulder 532 and/or base channel shoulder 534 will come close to or contact their respective feature on cartridge 100 to prevent cartridge 100 from bowing or deforming as the compressive force is applied to implantable adjunct 300.

Retainer 500 shown in FIGS. 5A-5D also includes one or more retention tabs 520 extending from retainer 500. Retention tabs 520 are outwardly deflectable upon seating into first jaw frame 204. Retention tabs 520 can keep retainer 500 connected to staple cartridge 100 until the cartridge/retainer is inserted into first jaw frame 204. For instance, retention tabs 520 can hook onto cartridge rails 118 of staple cartridge 100 (see FIGS. 2A and 2B). Upon insertion into first jaw frame 204, channel rails 208 of first jaw frame 204 will slip between retention tabs 520 and staple cartridge 100 to deflect them outwardly, thereby releasing them from cartridge rails 118 such that retainer 500 can be removed from staple cartridge 100.

Referring now to FIGS. 6A-6H, the example shows a staple cartridge and retainer system that can protect an adjunct during shipment of the staple cartridge and also provide a compressive force to the implantable adjunct. Unlike retainers 400 and 500 discussed above, retainer 600 in FIGS. 6A-6H does not include a base. Retainer cam 606 in this implementation is pointed inwardly toward staple cartridge 100, and retainer cam 606 engages with track 612 positioned within lug 212 of cartridge 100 (see FIG. 6C for detailed view of lug 212). Lug 212 can be an extension on elongate body 120; lug 212 fits within a corresponding slot 205 in first jaw frame 204 (see FIG. 3A toward the distal end of end effector 202). The implementation shown in FIGS. 6A-6H includes cam arm 624 pivotably attached to retainer 600. Retainer cam 606 is positioned on cam arm 624. Retainer 600 is moveable through a range of motion relative to elongate body 120 while retainer 600 is secured to elongate body 120. Retainer cam 606 moves through track 612 from a first cam position 614 to a second cam position 616 as retainer 600 is pressed toward elongate body 120 to compress implantable adjunct 300 against deck 108. To further illustrate, in the first cam position 614 (see FIG. 6E), retainer cam 606 is positioned such that retainer 600 is at a distance away from staple cartridge 100 and implantable adjunct 300 is not compressed. This can be the configuration in which the system is shipped. In the second cam position 616 (see FIG. 6F), retainer cam 606 is positioned such that retainer 600 moved toward staple cartridge 100 and implantable adjunct 300 becomes compressed. After retainer cam 606 passes the second cam position 616, retainer cam 606 moves toward track opening 618 such that retainer 600 can be removed from staple cartridge 100 (see FIG. 6G).

Retainer cam 606 can be attached to cam arm 624, for example via a pin 622 on the retainer 600 that engages with an aperture 626 on cam arm 624. Cam arm 624 is in turn pivotably attached to retainer 600. Actuating retainer cam 406, therefore, causes retainer cam 406 to pivot around pin 622 (see FIG. 6B). To facilitate retainer cam 606 moving through track 612, retainer 500 includes torsion spring 628 attached to retainer 600 and cam arm 624 (see FIG. 6D). Torsion spring 628 biases cam arm 624 toward track opening 618 of track 612. As retainer 600 is pressed toward staple cartridge 100, torsion spring 628 moves retainer cam 606 from first cam position 614 (see FIG. 6E), to second cam position 616 (see FIG. 6F), to track opening 618 (see FIG. 6G). In this embodiment, therefore, movement of retainer 600 with respect to implantable adjunct 300 is one dimensional to shield implantable adjunct 300 from shear forces of retainer 600 as implantable adjunct 300 is compressed. In other words, there is no sliding, axial movement for retainer 600 as there was described for retainers 400 and 500.

Referring again to FIG. 6A, staple cartridge 100 can include pan 114 disposed along a bottom surface 116 of elongate body 120. Pan 114 can be a rigid support along the length of elongate body 120 to prevent elongate body 120 from warping or deforming when compressive forces are applied to the cartridge. Referring now to FIG. 6H, retainer 600 also includes one or more retention tabs 620 extending from retainer 600. Retention tabs 620 are outwardly deflectable upon seating into first jaw frame 204. Retention tabs 620 can keep retainer 600 connected to staple cartridge 100 until the cartridge/retainer is inserted into first jaw frame 204. For instance, retention tabs 620 can hook onto cartridge rails 118 of staple cartridge 100 (see FIGS. 2A and 2B). Upon insertion into first jaw frame 204, channel rails 208 of first jaw frame 204 will slip between retention tabs 620 and staple cartridge 100 to deflect them outwardly, thereby releasing them from cartridge rails 118 such that retainer 600 can be removed from staple cartridge 100.

Figure 7A:
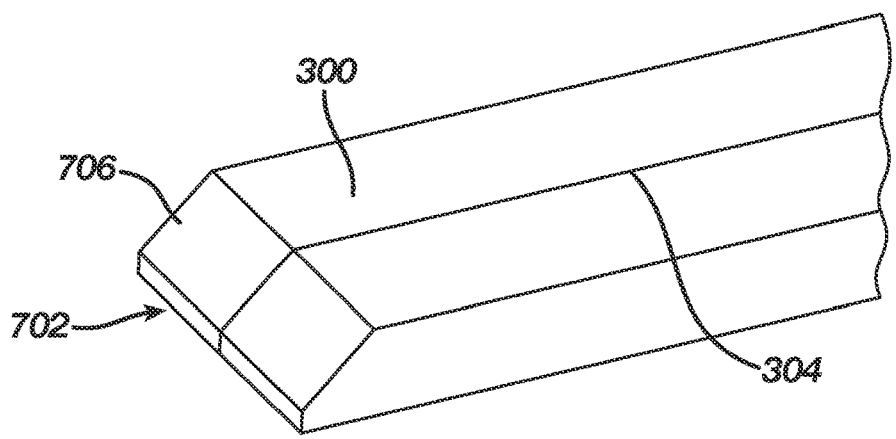
FIG. 7A shows the distal end of an implantable adjunct, according to aspects of the present disclosure.
Figure 7B:
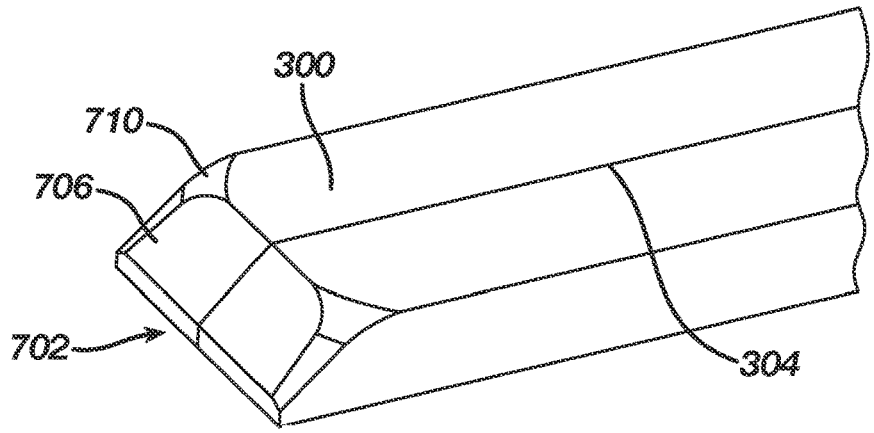
FIG. 7B shows the distal end of an implantable adjunct compressed to define a first lateral contour and a second lateral contour, according to aspects of the present disclosure.
Figure 7C:
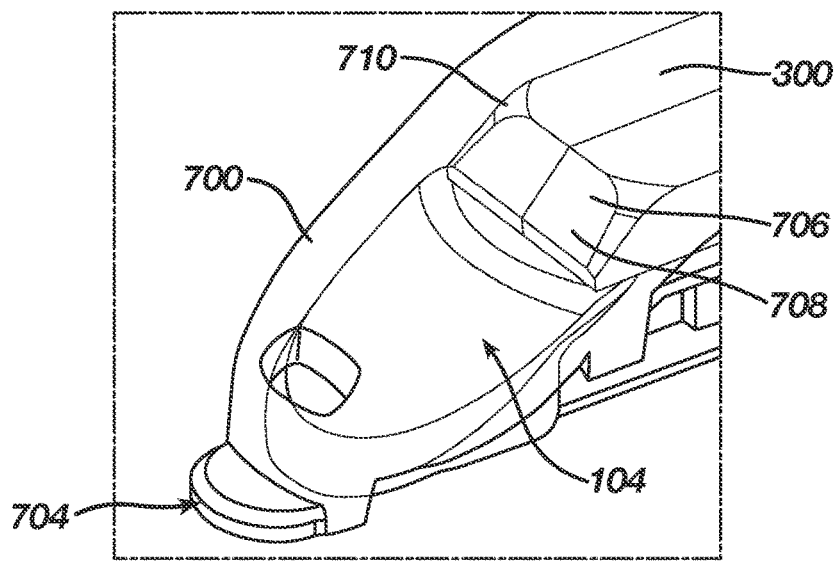
FIG. 7C is a partially transparent view of a staple cartridge, retainer, and adjunct, wherein the adjunct is compressed to define the first lateral contour and the second lateral contour of FIG. 7B, according to aspects of the present disclosure.

Referring now to FIGS. 7A-7C, the example shows various shapes of distal end 702 of implantable adjunct 300. As described above, an aspect of the present disclosure is to provide solutions to ensure the implantable adjunct 300 is properly adhered to deck 108 (FIG. 2B) so that it is not dislodged from deck 108 during shipment or, importantly, during surgery before the implantable adjunct 300 is positioned at the treatment site. Beveling distal end 702 of implantable adjunct 300 can help to prevent dislodging by providing a smooth profile for the adjunct as the cartridge navigates the tissue. In some instances, distal end 702 of implantable adjunct 300 can include a distal slant 706 (FIG. 7A) that can be cut into distal end 702 as the adjunct is manufactured. In an alternative embodiment, distal end 702 can be formed by a compressive force of a retainer (e.g., retainer 400, 500, 600, or 700). This compressive force can come from any of the embodiments described herein, wherein the respective retainer is pressed toward elongate body 120 to compress implantable adjunct 300. In other examples, the implantable adjunct 300 can be pre-compressed during shipment of the cartridge. In any example, once compression of removed from implantable adjunct 300, the adjunct can return to its manufactured, non-compressed state (for example after the adjunct has been implanted).

Referring now to the example adjunct shown in FIG. 7B, distal end 702 of implantable adjunct 300 defines a first lateral contour 708 and a second lateral contour 710. These two contour edges at corners of distal end 702 can further decrease the risk of dislodging implantable adjunct 300 as it traverses tissue to the treatment site by providing a smooth distal profile. In some examples, distal end 704 of retainer 700 (or any of retainers 400, 500, and 600 described herein) curves toward the implantable adjunct 300 and in a shape to define the contours. This shape of retainer 700 can compress distal end 702 of implantable adjunct 300 even when a retainer cam (e.g., retainer cam 406, 506, 606) is in the first cam position 414, 514, 614, i.e., before the respective retainer is actuated to compress implantable adjunct 300.

Figure 8A:
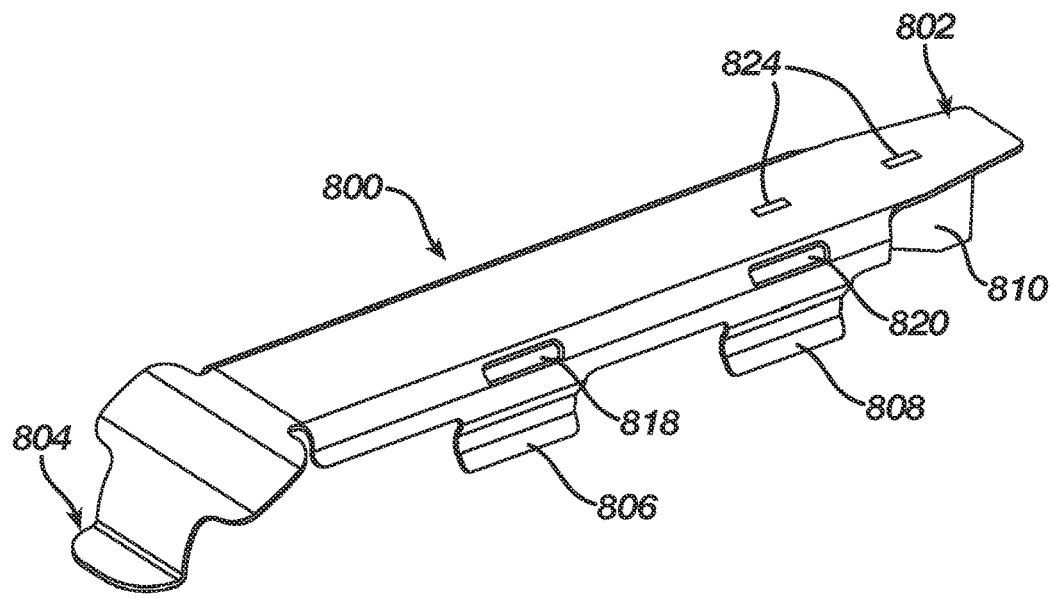
FIG. 8A is a perspective view of a clip-style retainer, according to aspects of the present disclosure.
Figure 8B:
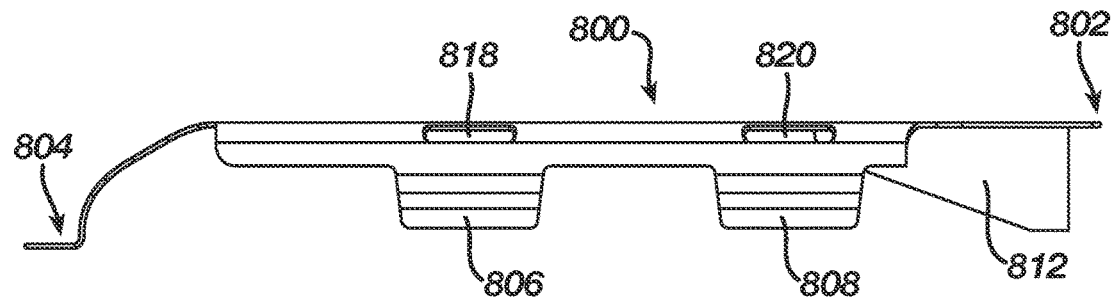
FIG. 8B is a side view of the clip-style retainer of FIG. 8A, according to aspects of the present disclosure.
Figure 8C:
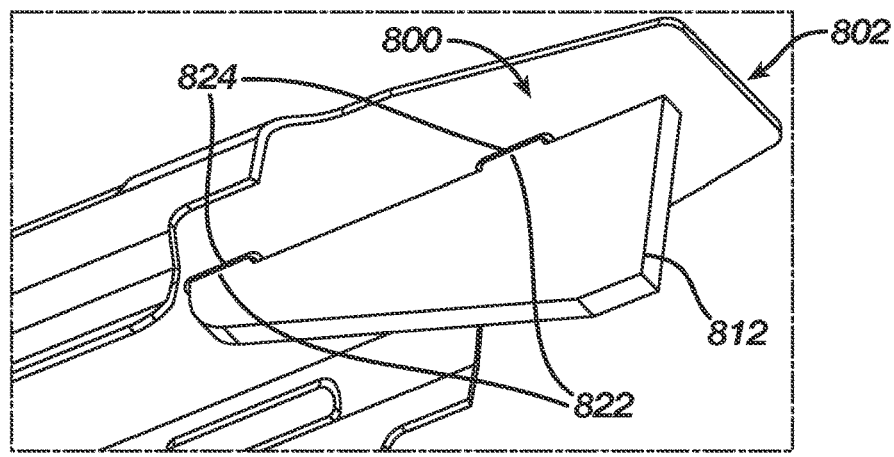
FIG. 8C is a detail view of a sled rib of the clip-style retainer of FIGS. 8A and 8B, according to aspects of the present disclosure.
Figure 8D:
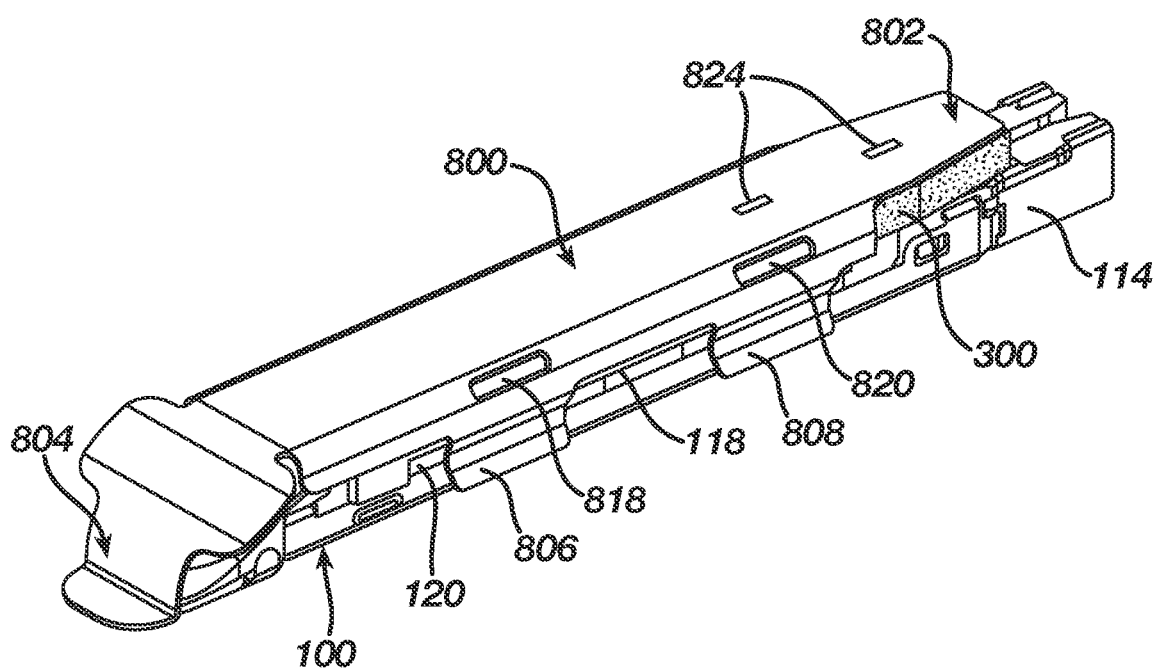
FIG. 8D shows a perspective view of the clip-style retainer of FIGS. 8A-8C attached to a staple cartridge, according to aspects of the present disclosure.

Referring now to FIGS. 8A-8E, the example system shown therein shows a clip-style retainer 800, according to aspects of the present disclosure. As shown in FIG. 8A, retainer 800 can cover implantable adjunct 300 from a proximal end 802 of the retainer, and a distal end 804 can curve toward elongate body 120 of staple cartridge 100 to protect a distal end of the cartridge. Retainer 800 includes first retention hook 806 and first retention hook 808 that extends toward elongate body 120 and can engage with cartridge rails 118 of staple cartridge 100. FIG. 8B is a side view of retainer 800 not being attached to staple cartridge 100, and FIG. 8D shows retainer 800 attached to staple cartridge 100. Retainer 800 includes sled rib 812 (FIG. 8C) that, when connected to staple cartridge 100, extends into sled groove 304 within length 350 of the implantable adjunct 300 (see FIG. 2C). Sled rib 812 can abut a sled (see sled 216 in FIG. 9) of the staple cartridge 100 and prevent it from moving distally (and thus firing staples) prematurely. Sled rib 812 can be affixed to retainer 800 by weld tabs 822 extending from sled rib 812 which extend into weld slots 824 on retainer 800. Weld tabs 822 can be welded to retainer 800 when the tabs are inserted into their respective weld slots 824.

Figure 8E:
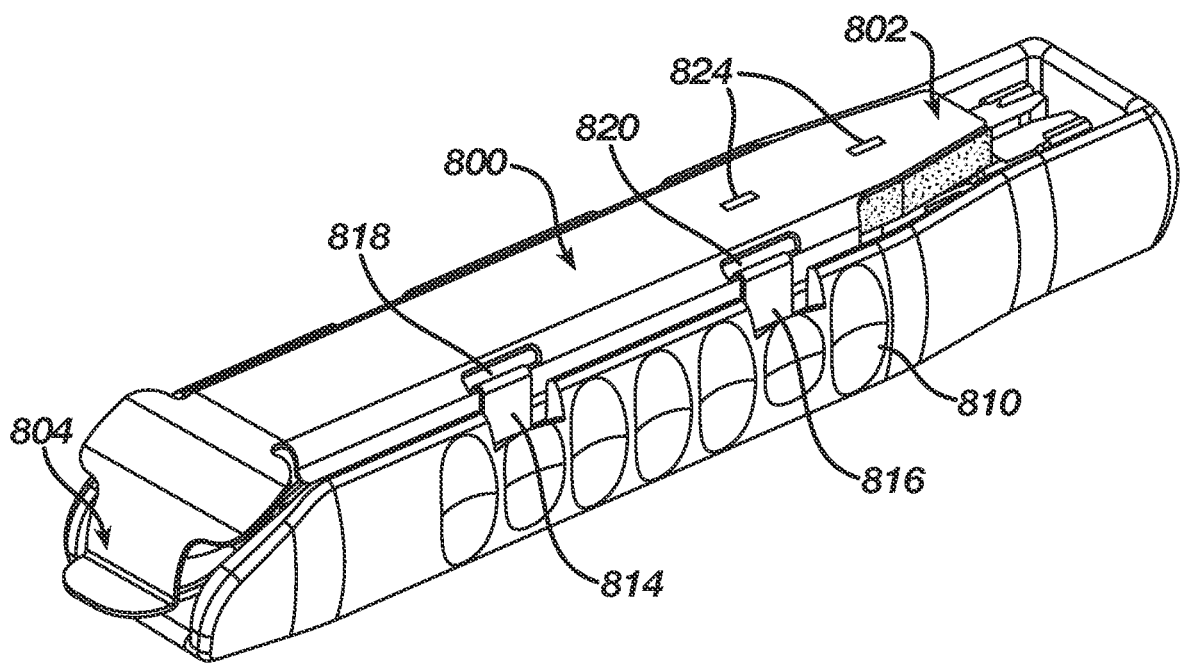
FIG. 8E shows a perspective view of the clip-style retainer of FIG. 8D attached to a base, according to aspects of the present disclosure.

The system shown in FIGS. 8A-8E includes base 810. As shown in FIG. 8E, base 810 includes hooks, i.e., first hook 814 and second hook 816. First hook 814 and second hook 816 can loop over to engage with openings in retainer 800, i.e., first hook opening 818 and second hook opening 820, respectively. First hook 814 and second hook 816 are biased outwardly, so when a force is applied to retainer 800 to move the retainer toward base 810, the retainer both compresses implantable adjunct 300 and allows first hook 814 and second hook 816 to disengage from their respective hook openings and spring outwardly, releasing retainer 800 and allowing base 810 to be detached and removed from retainer 800.

Figure 9:
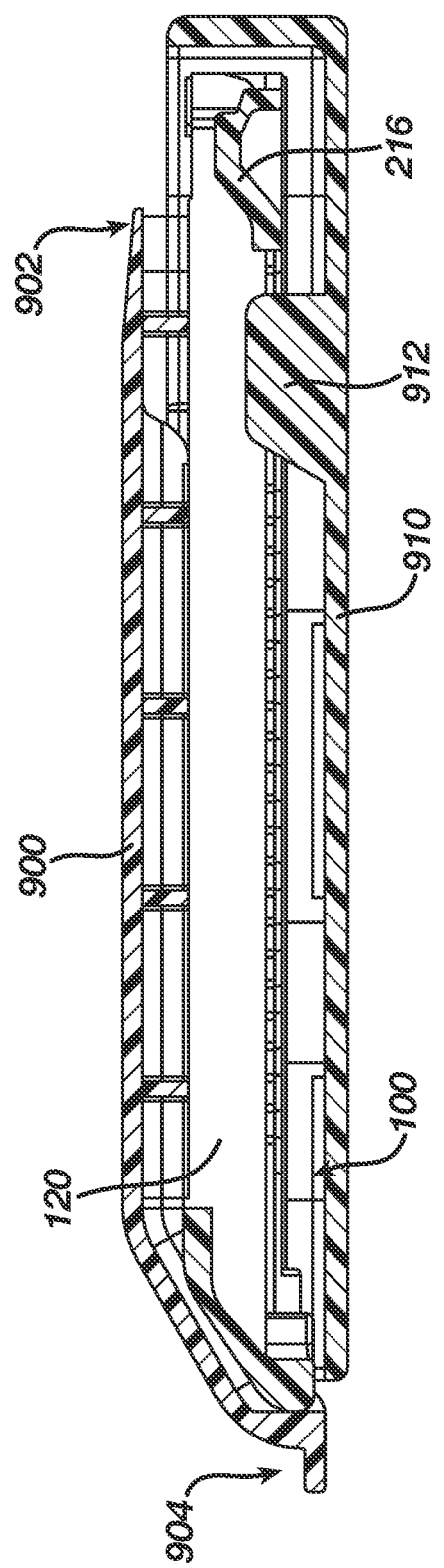
FIG. 9 is a cutaway view of a retainer and a base, the base having a base rib, according to aspects of the present disclosure.

FIG. 9 is a cutaway view of retainer 900 and base 910. Base 910 includes base rib 912. Retainer 900 is substantially similar to retainer 800 described above, but retainer 900 does not include a rib (e.g., sled rib 812). Instead, base rib 912 extends from the bottom surface of base 910, through staple cartridge 100, and into sled groove 304 (see FIG. 2C). Base rib 912 can abut sled 216 of staple cartridge 100 and prevent the sled from moving distally (and thus firing staples) prematurely. Sled rib 812 can be affixed to retainer 800 by weld tabs 822 extending from sled rib 812 which extend into weld slots 824 on retainer 800. Weld tabs 822 can be welded to retainer 800 when the tabs are inserted into their respective weld slots 824.

Figure 10:
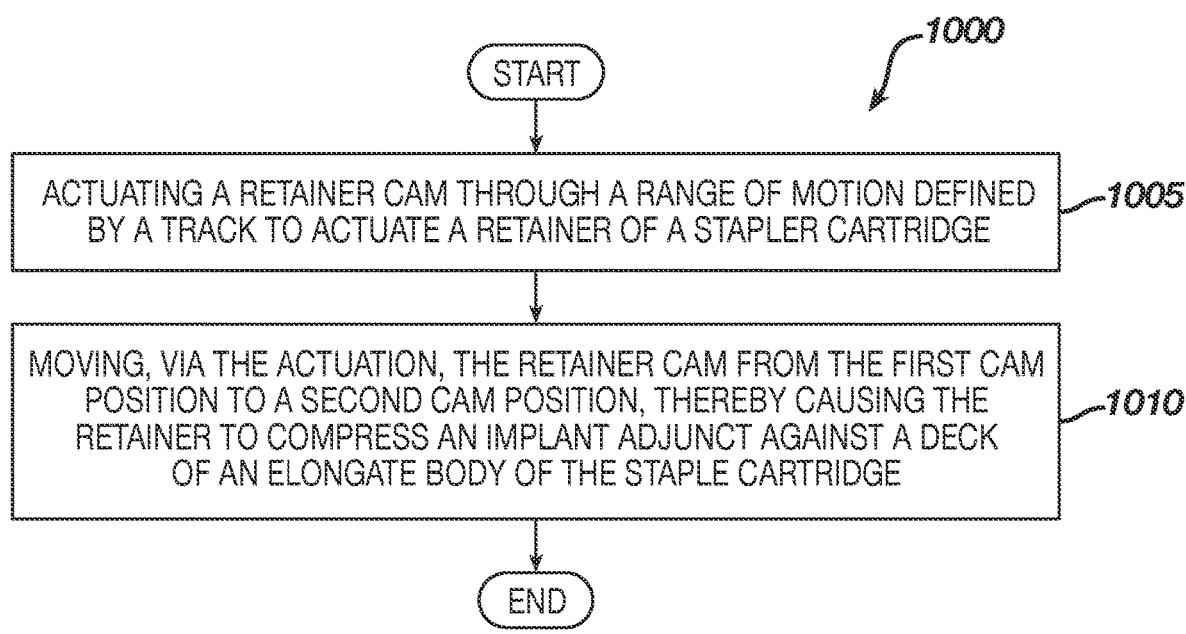
FIG. 10 is a flowchart of a method of causing a retainer to compress an implantable adjunct against a deck of an elongated body of a staple cartridge, according to aspects of the present disclosure.

FIG. 10 is a flowchart of a method 1000 of causing a retainer to compress implantable adjunct 300 against deck 108 of elongated body 120 of staple cartridge 100, according to aspects of the present disclosure. Method 1000 can be performed to on and of the retainers shown in FIGS. 4A-7C (e.g., retainers 400, 500, 600, and 700). Method 1000 includes actuating 1005 a retainer cam (e.g., retainer cam 406, 506, 606) through a range of motion defined by a track (e.g., track 412, 512, 612) to actuate a retainer (e.g., retainers 400, 500, 600, 700) of staple cartridge 100. Method 1000 includes moving 1010, via the actuation in step 1005, the retainer cam 406, 506, 606 from a first cam position 414, 514, 614 to second cam position 416, 516, 616, thereby causing the retainer 400, 500, 600, 700 to compress implantable adjunct 300 against deck 108 of elongate body 120 of the staple cartridge.

Method 1000 can end after step 1010, or other steps can be performed according to the embodiments described herein. For example, method 1000 can include actuating actuator 422 comprising actuator ramp 428 such that actuator ramp 428 engages with retainer ramp 408 on retainer 400, thereby causing retainer cam 406 to actuate through the range of motion defined by track 412. Method 1000 can include grasping staple cartridge 100 by base 410, 510, wherein base 410, 510 remains static with respect to elongated body 120 while actuating retainer 400, 500 through the range of motion.

Examples of the present disclosure can be implemented by any of the following numbered clauses:

Clause 1: A staple cartridge (100), comprising: an elongate body (120), the elongate body (120) comprising a deck (108), the elongate body (120) defining a plurality of staple pockets (110), each of the staple pockets (110) accessible via an opening (112) defined by the deck (108); an implantable adjunct (300) removably secured to the deck (108); a track (412, 512, 612); and a retainer (400, 500, 600, 700) removably securable to the elongate body (120) and comprising a retainer cam (406, 506, 606) engageable with the track (412, 512, 612), the retainer (400, 500, 600, 700) movable through a range of motion relative to the elongate body (120) while the retainer (400, 500, 600, 700) is secured to the elongate body (120), the track (412, 512, 612) further defining a movement path for the retainer (400, 500, 600, 700) with respect to the elongate body (120), with the retainer (400, 500, 600, 700) secured to the elongate body (120), and the implantable adjunct (300) positioned intermediate the retainer (400, 500, 600, 700) and the elongate body (120), a movement of the retainer cam (406, 506, 606) through the track (412, 512, 612) from a first cam position (414, 514, 614) to a second cam position (416, 516, 616) moves the retainer (400, 500, 600, 700) toward the elongate body (120) thereby compressing the implantable adjunct (300) against the deck (108) of the elongate body (120).

Clause 2: The staple cartridge (100) of Clause 1 further comprising a base (410, 510) comprising the track (412, 512, 612), wherein the base (410, 510) is positioned adjacent the elongate body (120) during the movement of the retainer cam (406, 506, 606) through the track (412, 512, 612).

Clause 3: The staple cartridge (100) of Clause 2, wherein the base (410, 510) is stationary with respect to the elongate body (120) during the movement of the retainer cam (406, 506, 606) through the track (412, 512, 612) from the first cam position (414, 514, 614) to the second cam position (416, 516, 616).

Clause 4: The staple cartridge (100) of Clause 2 or 3 further comprising an actuator (422) positioned proximate a distal end (404) of the retainer (400) during the movement of the retainer cam (406) through the track, wherein actuation of the actuator (422) causes the retainer cam (406) to move through the track (412) and further causes the retainer (400) to compress the implantable adjunct (300) and slide axially with respect to a longitudinal axis (106) of the elongate body (120).

Clause 5: The staple cartridge (100) of Clause 4, wherein the actuator (422) comprises an actuator ramp (428), and the retainer (400) comprises a retainer ramp (408) at its distal end (404) that is slidably engageable with the actuator ramp (428) upon actuation of actuator (422), causing the retainer (400) to slide axially with respect to a longitudinal axis (106) of the elongate body (120).

Clause 6: The staple cartridge (100) of Clause 4 or 5, wherein the actuator (422) comprises an actuator cam (424), the base (410) comprises an actuator track (426), and movement of the actuator (422) is constrained by engagement of the actuator cam (424) with the actuator track (426).

Clause 7: The staple cartridge (100) of Clause 2, wherein the base (510) comprises a base grip surface (524), and the retainer (500) comprises a retainer grip surface (522).

Clause 8: The staple cartridge (100) of any one of Clauses 2 to 7, wherein the base (410, 510) comprises at least one of a base lug shoulder (432, 532) and a base channel shoulder (434, 534).

Clause 9: The staple cartridge (100) of Clause 1 further comprising a lug (212) positioned proximate a distal end (104) of the elongate body (120), wherein the track (612) is positioned within the lug (212), and the retainer cam (606) is aligned inwardly toward the track (612).

Clause 10: The staple cartridge (100) of Clause 9, further comprising a cam arm (624) pivotably attached to the retainer (600), wherein the retainer cam (606) is positioned on the cam arm (624).

Clause 11: The staple cartridge (100) of Clause 10, further comprising a torsion spring (628) attached to the retainer (600) and the cam arm (624), the torsion spring (628) biasing the cam arm (624) toward a track opening (618) of the track (612).

Clause 12: The staple cartridge (100) of any of Clauses 9 to 11, wherein movement of the retainer (400, 500, 600, 700) with respect to the implantable adjunct (300) is substantially one dimensional to shield the implantable adjunct (300) from shear forces of the retainer (400, 500, 600, 700) as the implantable adjunct (300) is compressed by the movement of the retainer cam (406, 506, 606) through the track (412, 512, 612) from the first cam position (414, 514, 614) to the second cam position (416, 516, 616).

Clause 13: The staple cartridge (100) of any of Clauses 9 to 12 further comprising: at least one cartridge rail (118) extending along the elongate body (120); and one or more retention tabs (620) engageable with the at least one cartridge rail (118) and deflectable upon insertion into a channel (206) of an end effector (202).

Clause 14: The staple cartridge (100) of any one of the preceding Clauses, wherein the retainer (400, 500, 600, 700) is secured to the staple cartridge (100) when the retainer cam (406, 506, 606) is in the first cam position (414, 514, 614) and the second cam position (416, 516, 616), and is removable from the staple cartridge (100) when the retainer cam (406, 506, 606) has moved past the second cam position (416, 516, 616) and to a track opening (418, 518, 618).

Clause 15: The staple cartridge (100) of any one of the preceding Clauses, wherein a distal end (704) of the retainer (400, 500, 600, 700) curves toward the implantable adjunct (300) and compresses a distal end (702) of the implantable adjunct (300) when the retainer cam (406, 506, 606) is in the first cam position (414, 514, 614), the compression of the distal end (702) of the implantable adjunct (300) defining a first lateral contour (708) and a second lateral contour (710).

Clause 16: A method of causing a retainer (400, 500, 600, 700) to compress an implantable adjunct (300) against a deck (108) of an elongated body (120) of a staple cartridge (100), the method comprising: actuating a retainer cam (406, 506, 606) through a range of motion defined by a track (412, 512, 612) to actuate a retainer (400, 500, 600, 700) of a staple cartridge (100); and moving, via the actuation, the retainer cam (406, 506, 606) from a first cam position (414, 514, 614) to a second cam position (416, 516, 616), thereby causing the retainer (400, 500, 600, 700) to compress an implantable adjunct (300) against a deck (108) of an elongate body (120) of the staple cartridge (100).

Clause 17: The method of Clause 16 further comprising actuating an actuator (422) comprising an actuator ramp (428) such that the actuator ramp (428) engages with a retainer ramp (408) on the retainer (400), thereby causing the retainer cam (406) to actuate through the range of motion defined by the track (412).

Clause 18: The method of Clause 16 or 17, further comprising grasping the staple cartridge (100) by a base (410, 510), wherein the base (410, 510) remains static with respect to the elongated body (120) while actuating the retainer (400, 500, 600, 700) through the range of motion.

Clause 19: The method of Clause 16, wherein actuating a retainer cam (406, 506, 606) causes the retainer cam (406, 506, 606) to pivot around a pin (622).

Clause 20: The method of Clause 19, wherein a movement of the retainer (600) with respect to the implantable adjunct (300) is one dimensional to shield the implantable adjunct (300) from shear forces of the retainer (600) as the implantable adjunct (300) is compressed.

The invention is not necessarily limited to the examples described, which can be varied in construction and detail. The terms "distal" and "proximal" are used throughout the preceding description and are meant to refer to a positions and directions relative to the handle of surgical instrument 200. As such, "distal" or distally" refer to a position distant to or a direction away from the handle of surgical instrument 200 (i.e., a direction toward a patient). Similarly, "proximal" or "proximally" refer to a position near or a direction towards the handle of surgical instrument 200 (i.e., toward an operator of the handle). Furthermore, the singular forms "a," "an," and "the" include plural referents unless the context clearly dictates otherwise. Furthermore, the use of "couple", "coupled", or similar phrases should not be construed as being limited to a certain number of components or a particular order of components unless the context clearly dictates otherwise.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±10% of the recited value, e.g., "about 90%" may refer to the range of values from 80.1% to 99.9%.

In describing example embodiments, terminology has been resorted to for the sake of clarity. As a result, not all possible combinations have been listed, and such variants are often apparent to those of skill in the art and are intended to be within the scope of the claims which follow. It is intended that each term contemplates its broadest meaning as understood by those skilled in the art and includes all technical equivalents that operate in a similar manner to accomplish a similar purpose without departing from the scope and spirit of the invention. It is also to be understood that the mention of one or more steps of a method does not preclude the presence of additional method steps or intervening method steps between those steps expressly identified. Similarly, some steps of a method can be performed in a different order than those described herein without departing from the scope of the disclosed technology.

What is claimed is:

1. A staple cartridge, comprising:
   an elongate body, the elongate body comprising a deck, the elongate body defining a plurality of staple pockets, each of the staple pockets accessible via an opening defined by the deck;
   an implantable adjunct removably secured to the deck;
   a track; and
   a retainer removably securable to the elongate body and comprising a retainer cam engageable with the track, the retainer movable through a range of motion relative to the elongate body while the retainer is secured to the elongate body, the track further defining a movement path for the retainer with respect to the elongate body, with the retainer secured to the elongate body, and the implantable adjunct positioned intermediate the retainer and the elongate body,
   a movement of the retainer cam through the track from a first cam position to a second cam position moves the retainer toward the elongate body thereby compressing the implantable adjunct against the deck of the elongate body.

2. The staple cartridge of claim 1 further comprising a base comprising the track, wherein the base is positioned adjacent the elongate body during the movement of the retainer cam through the track.

3. The staple cartridge of claim 2, wherein the base is stationary with respect to the elongate body during the movement of the retainer cam through the track from the first cam position to the second cam position.

4. The staple cartridge of claim 2 further comprising an actuator positioned proximate a distal end of the retainer during the movement of the retainer cam through the track, wherein actuation of the actuator causes the retainer cam to move through the track and further causes the retainer to compress the implantable adjunct and slide axially with respect to a longitudinal axis of the elongate body.

5. The staple cartridge of claim 4, wherein the actuator comprises an actuator ramp, and the retainer comprises a retainer ramp at its distal end that is slidably engageable with the actuator ramp upon actuation of actuator, causing the retainer to slide axially with respect to a longitudinal axis of the elongate body.

6. The staple cartridge of claim 4, wherein the actuator comprises an actuator cam, the base comprises an actuator track, and movement of the actuator is constrained by engagement of the actuator cam with the actuator track.

7. The staple cartridge of claim 2, wherein the base comprises a base grip surface, and the retainer comprises a retainer grip surface.

8. The staple cartridge of claim 2, wherein the base comprises at least one of a base lug shoulder and a base channel shoulder.

9. The staple cartridge of claim 1 further comprising a lug positioned proximate a distal end of the elongate body, wherein the track is positioned within the lug, and the retainer cam is aligned inwardly toward the track.

10. The staple cartridge of claim 9, further comprising a cam arm pivotably attached to the retainer, wherein the retainer cam is positioned on the cam arm.

11. The staple cartridge of claim 10, further comprising a torsion spring attached to the retainer and the cam arm, the torsion spring biasing the cam arm toward a track opening of the track.

12. The staple cartridge of claim 9, wherein movement of the retainer with respect to the implantable adjunct is substantially one dimensional to shield the implantable adjunct from shear forces of the retainer as the implantable adjunct is compressed by the movement of the retainer cam through the track from the first cam position to the second cam position.

13. The staple cartridge of claim 9 further comprising:
at least one cartridge rail extending along the elongate body; and
one more retention tabs engageable with the at least one cartridge rail and deflectable upon insertion into a channel of an end effector.

14. The staple cartridge of claim 1, wherein the retainer is secured to the staple cartridge when the retainer cam is in the first cam position and the second cam position, and is removable from the staple cartridge when the retainer cam has moved past the second cam position and to a track opening.

15. The staple cartridge of claim 1, wherein a distal end of the retainer curves toward the implantable adjunct and compresses a distal end of the implantable adjunct when the retainer cam is in the first cam position, the compression of the distal end of the implantable adjunct defining a first lateral contour and a second lateral contour.

16. A method of causing a retainer to compress an implantable adjunct against a deck of an elongated body of a staple cartridge, the method comprising:
actuating a retainer cam through a range of motion defined by a track to actuate a retainer of a staple cartridge; and
moving, via the actuation, the retainer cam from a first cam position to a second cam position, thereby causing the retainer to compress an implantable adjunct against a deck of an elongate body of the staple cartridge.

17. The method of claim 16 further comprising actuating an actuator comprising an actuator ramp such that the actuator ramp engages with a retainer ramp on the retainer, thereby causing the retainer cam to actuate through the range of motion defined by the track.

18. The method of claim 16, further comprising grasping the staple cartridge by a base, wherein the base remains static with respect to the elongated body while actuating the retainer through the range of motion.

19. The method of claim 16, wherein actuating a retainer cam causes the retainer cam to pivot around a pin.

20. The method of claim 19, wherein a movement of the retainer with respect to the implantable adjunct is one dimensional to shield the implantable adjunct from shear forces of the retainer as the implantable adjunct is compressed.

* * * * *